US00PP10766P

United States Patent [19]

Dümmen

[11] Patent Number: Plant 10,766

[45] Date of Patent: Jan. 26, 1999

[54] GERANIUM PLANT NAMED 'DUEBIA'

[75] Inventor: Marga Dümmen, Rheinberg-Eversael, Germany

[73] Assignee: Dummen Jungpflanzenkulturen, Rheinberg-Eversael, Germany

[21] Appl. No.: 699,082

[22] Filed: Aug. 19, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,392 12/1990 Schumann ..... Plt./87.12

OTHER PUBLICATIONS

GTITM UPOVROM Citation for 'Duebia' as per DE PBR PEL 00760, Mar. 4, 1994.

GTITM UPOVROM Citation for 'Duebia' as per NL PBR GRM 0314, Nov. 15, 1994.

GTITM UPOVROM Citation for 'Dueimbia' as per DE PBR PEL 00970, Dec. 18, 1995.

*Primary Examiner*—Howard J. Locker
*Assistant Examiner*—Kent L. Bell
*Attorney, Agent, or Firm*—C. A. Whealy

[57] ABSTRACT

A new and distinct cultivar of Geranium plant named 'Duebia', characterized by its semi-double clear white flowers; numerous flowers per umbel; compact to medium plant size; medium green leaf color; medium-sized umbels; medium to large flower size; and freely branching plant habit.

1 Drawing Sheet

The present invention relates to a new and distinct cultivar of Geranium plant, botanically known as *Pelargonium× hortorum*, and named 'Duebia'. It is anticipated that the plant of this application will be marketed under the name "HWD Bianca". The new cultivar is a product of a planned breeding program conducted by the inventor in Rheinberg, Germany. The objective of the breeding program was to develop a new freely branching, semi-double geranium with clear white semi-double flowers. The new cultivar originated from a cross made by the inventor of the proprietary selection 86-45-3 as the male or pollen parent with the proprietary selection 86-24-5 as the female or seed parent. The cultivar 'Duebia' was discovered and selected by the inventor as a flowering plant within the progeny of the stated cross in a controlled environment in Rheinberg, Germany, in 1989. Asexual reproduction of the new cultivar by terminal cuttings taken at Rheinberg, Germany, has shown that the unique features of this new Geranium are stable and reproduced true to type in successive generations of asexual reproduction. The following traits have been repeatedly observed and are determined to be the unique characteristics of 'Duebia'. These characteristics in combination distinguish 'Duebia' as a new and distinct cultivar:

1. Semi-double clear white flowers.
2. Numerous flowers per umbel.
3. Compact to medium plant size.
4. Medium green leaf color.
5. Medium-sized umbels.
6. Medium to large flower size.
7. Freely branching.

Incomparison to the parent selection 86-45-3, plants of the new Geranium have larger flowers and lighter green foliage. In comparison to the parent selection 86-24-5, plants of the new Geranium have larger umbels. The new Geranium is similar in petal color to the cultivar 'Fisbal' (disclosed in U.S. Plant Pat. No. 7,392). Compared to plants of the cultivar 'Fisbal', plants of the new Geranium are larger and more freely branching. In addition, foliage of plants of the new Geranium have a less pronounced zonation pattern and the leaf margin is not as deeply crenated as plants of the cultivar 'Fisbal'.

The accompanying colored photograph illustrates the overall appearance of the new cultivar, showing the colors as true as it is reasonably possible to obtain in colored reproductions of this type. The photograph comprises a top perspective view of a typical potted plant of 'Duebia' with one plant in a 10-cm container. Foliage color in the photograph appears darker than the actual due to light reflectance.

The cultivar 'Duebia' has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24°C. and night temperatures of 18 to 20°C. and light levels of 45,000 to 60,000 lux. Plants were grown in 10cm pots with one plant per pot. In the following description, color references are made to The Royal Horticultural Society Colour Chart except where general terms of ordinary dictionary significance are used.

Classification:

*Botanical.*—*Pelargonium×hortorum.*

*Commercial.*—Zonal Geranium.

*Cultivar.*—'Duebia'.

Parentage:

*Male parent.*—Proprietary selection 86-45-3.

*Female parent.*—Proprietary selection 86-24-5.

Propagation:

*Type cutting.*—Terminal cuttings.

*Time to initiate and develop roots.*—Summer: 27°C., 21 days. Winter: 20°C., 28 days.

Plant description:

*General appearance.*—Rounded; compact to medium plant size; upright to slightly spreading; and freely branching. Plants grown in 10-cm containers are usually about 30 cm in height and 33 cm in diameter.

*Foliage description.*—Arrangement: Mostly opposite, some alternate. Shape: Orbicular with rounded or slightly clefted apex and cordate base. Size: Length: About 7.5 cm. Width: About 9 cm. Texture: Velvety, pubescent on abaxial and adaxial surfaces. Margin: Crenate. Zonation: Slight, 1.5 to 2 cm in width and 2.5 to 3 cm from margin. Color: Young foliage, adaxial surface: 147B. Young foliage, abaxial surface: 147B. Mature foliage, adaxial surface: 147B. Mature foliage, abaxial surface: 147B. Veins, adaxial surface: 144A. Veins, abaxial surface: 147C.

Zonation, adaxial surface only: 147A. Venation pattern: Palmate. Petiole: Length: 8 to 9 cm. Diameter: About 2 mm. Color: 144A.

Flowering description:

*Flowering habit.*—Freely flowering. Flowers arranged in umbels.

*Natural flowering season.*—Year-round.

*Flowers borne.*—Flowers buds develop in apical leaf axils. Umbels are displayed above the foliage.

*Quanity of inflorescences.*—Very floriferous; usually about 5 open umbels and at least 6 developing umbels per plant at one time.

*Umbels.*—Form: Rounded. Diameter: About 12 cm. Depth (height): About 7 cm.

*Flowers.*—Form: Semi-double Shape: Rounded. Quantity of flowers per umbel: About 36. Diameter: 4.5 to 5 cm.

*Petals.*—Shape: Obovate with rounded apex. Arrangement: Rosette, overlapping. Quantity: About 6. Aspect: Flat. Size: Length: About 2.5 cm. Width: About 2.5 cm. Texture: Satiny, smooth. Margin: Entire. Color: When opening, adaxial surface: Whiter than 155D. When opening, abaxial surface: Whiter than 155D. Fully open, adaxial surface: Whiter than 155D. Fully open, abaxial surface: Whiter than 155D.

*Petaloids.*—Shape: Irregular, sometimes twisted, generally obovate with rounded or clefted apex. Arrangement: Rosette, overlapping. Quantity: 1 to 4. Size: Length: 1 to 1.5 cm. Width: 3 to 10 mm. Texture: Satiny, smooth. Margin: Entire. Color: When opening, adaxial surface: Whiter than 155D. When opening, abaxial surface: Whiter than 155D. Fully open, adaxial surface: Whiter than 155D. Fully open, abaxial surface: Whiter than 155D.

*Peduncle* (*umbel stem*).—Angle: Erect to slightly bent near apex. Length: 18 to 21 cm. Pubescence: Fine. Color: 144A.

*Pedicel* (*individual flower stem*).—Angle: Erect, rigid. Length: 3 to 3.4 cm. Pubescence: Fine. Color: 144A.

*Flower bud.*—Shape: Ovoid. Length: About 1.5 cm. Diameter: About 8 mm. Color: 155B.

*Sepals.*—Arrangement: Rosette. Quantity: 5. Size: Length: About 1 cm. Width: 2 to 3 mm. Shape: Acuminate with apiculate apex. Texture: Velvety. Margin: Entire. Color: Adaxial surface: 144A. Abaxial surface: 144A.

*Reproductive organs.*—Androecium: Stamen number: 11 to 12. Anther size: About 2 mm. Anther color: 33D. Pollen color: 28A. Gynoecium: Pistil number: 1. Pistil length: About 1 cm. Stigma shape: Decurrent. Stigma color: 155A/145D Style length: About 4 mm. Style color: 155A/145D.

*Ploidy level: Tetraploid.*

Disease resistance: No fungal, bacterial nor viral problems observed under commercial conditions.

Seed development: Seed production is very rarely observed.

It is claimed:

1. A new and distinct cultivar of Geranium plant named 'Duebia', as illustrated and described.

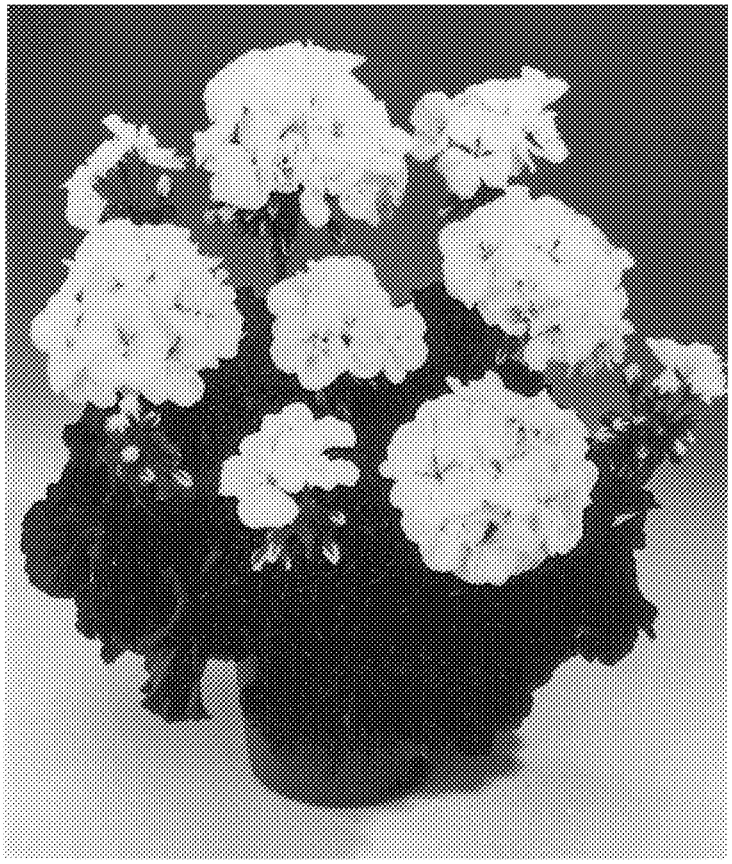

* * * * *